United States Patent
Koch

(10) Patent No.: US 9,408,769 B2
(45) Date of Patent: Aug. 9, 2016

(54) EXTENSION DEVICE

(75) Inventor: Guido Koch, Karlsruhe (DE)

(73) Assignee: MAQUET GMBH, Rastatt (DE)

( * ) Notice: Subject to any disclaimer, the term of this patent is extended or adjusted under 35 U.S.C. 154(b) by 675 days.

(21) Appl. No.: 13/369,466

(22) Filed: Feb. 9, 2012

(65) Prior Publication Data
US 2012/0204885 A1 Aug. 16, 2012

(30) Foreign Application Priority Data

Feb. 10, 2011 (DE) .......................... 20 2011 000 308

(51) Int. Cl.
| | | |
|---|---|---|
| A61G 13/12 | (2006.01) | |
| A61F 5/042 | (2006.01) | |
| A61G 13/10 | (2006.01) | |
| A61B 17/60 | (2006.01) | |

(52) U.S. Cl.
CPC ............ *A61G 13/1245* (2013.01); *A61F 5/042* (2013.01); *A61G 13/101* (2013.01); *A61B 17/60* (2013.01)

(58) Field of Classification Search
USPC ...................... 128/845–846, 882; 5/619–621, 5/623–624; 602/32, 35; 606/54, 57
See application file for complete search history.

(56) References Cited

U.S. PATENT DOCUMENTS

| | | | |
|---|---|---|---|
| 4,146,793 A * | 3/1979 | Bergstrom et al. ........... | 378/161 |
| 4,940,218 A | 7/1990 | Akcelrod | |
| 5,645,079 A | 7/1997 | Zahiri et al. | |
| 2006/0185090 A1 | 8/2006 | Jackson | |
| 2007/0156122 A1* | 7/2007 | Cooper ............................. | 606/1 |
| 2007/0265635 A1* | 11/2007 | Torrie et al. .................... | 606/105 |
| 2011/0023893 A1* | 2/2011 | Striggow et al. .............. | 128/882 |

FOREIGN PATENT DOCUMENTS

| | | |
|---|---|---|
| CN | 101700656 A | 5/2010 |
| DE | 20 2009 013 905 U1 | 2/2010 |
| JP | 2009525767 A | 7/2009 |
| WO | 2009062324 A1 | 5/2009 |

OTHER PUBLICATIONS

European Patent Application Search Report for European Patent Application No. EP12154697.2 dated May 30, 2012.
The English Translation of Office Action and Search Report for Chinese Patent Application No. CN201210028864.5 dated Dec. 17, 2013.
English Translation of a Notification of Provisional Refusal for Japanese Patent Application JP2012024986 dated Apr. 16, 2013.

* cited by examiner

*Primary Examiner* — Ophelia A Hawthorne

(57) ABSTRACT

An extension device includes a patient support surface and an extension beam (16) that can be connected via an interface (14) to the patient support surface and that has a holder for a feed rod arrangement. The patient support surface has at least two longitudinal beams (10) parallel to each other that carry a pelvic support plate. The interface (14) includes a coupling part (36) on the support surface side and a coupling part (38) on the beam side rigidly connected to the extension beam (16). The coupling part (36) on the support surface side on one of the longitudinal beams (10) is supported such that it can pivot about an axis perpendicular to the pelvic support plate, and whereby the coupling part (36) on the support surface side can be locked by a locking device, which may be actuated by remote actuation, against a rotation about its pivot axis relative to the longitudinal beam (10).

20 Claims, 5 Drawing Sheets

US 9,408,769 B2

EXTENSION DEVICE

CROSS REFERENCE TO RELATED APPLICATIONS

Applicant hereby claims foreign priority benefits under U.S.C. §119 from German Utility Model Application No. 20 2011 000 308.6 filed on Feb. 10, 2011, the contents of which are incorporated by reference herein.

TECHNICAL FIELD

The invention relates to an extension device comprising a patient support surface and an extension beam that can be connected on its one end via an interface to the patient support surface and that has a holder for a feed rod arrangement on its other end, whereby the patient support surface has at least two longitudinal beams parallel to each other that carry a pelvic support plate.

BACKGROUND OF THE INVENTION

The task of an extension device is to support the leg in a freely accessible manner in orthopedic surgeries such as, e.g., repositioning of bone fractures in the leg area or hip endoprostheses. To this end the patient's foot is received in a so-called extension shoe to the sole of which a feed rod unit is adapted. A tractive force can be applied via this feed rod unit in the longitudinal direction of the leg in order, for example to bring the broken edges of the bone into their original position during the repositioning, during which the leg should be able to pivot in and out.

An extension device of the initially cited type is known, for example, from the German utility model 20 2009 013 905 U1. In it, the patient support surface of an operation table is coupled to an orthopedic adapter that has interfaces for the coupling of an extension beam in the prolongation of the longitudinal beams of the patient support surface. To this end the extension beam has a coupling element with which it can be suspended on the interface parallel to the longitudinal direction of a longitudinal beam of the patient support surface. The coupling element has an articulation with a vertical articulation axis about which the extension beam can pivot in a horizontal plane. This solution has the disadvantage that the control element for locking the articulation in the immediate vicinity of the pelvic plate underneath it and in a hip operation therefore lies in the immediate operating area. This makes the control difficult when the patient's leg is to be pivoted during the operation.

Another solution is known from U.S. Pat. No. 4,940,218 A. This publication shows an orthopedic operating table with two permanently articulated extension beams that can pivot in a horizontal plane as well as in a vertical plane. The extension beams can not be separated.

SUMMARY OF THE INVENTION

The invention has the basic task of indicating an extension device of the initially cited type that is constructed in such a manner that the extension beam can be conveniently coupled and decoupled as required and furthermore can be conveniently pivoted without this disturbing the operating surgeon or endangering the sterility of the operation location.

The invention solves this task in that the interface comprises a coupling part on the support surface side and comprises a coupling part on the beam side and rigidly connected to the extension beam, that the coupling part on the support surface side on one of the longitudinal beams of the patient support surface is supported in such a manner that it can pivot about an axis perpendicular to the pelvic support plate, and that the coupling part on the support surface side can be locked by a locking device against a rotation about its pivot axis with respect to the longitudinal beam, which locking device can be actuated by a remote actuation.

As a result of the fact that the coupling part on the support surface side is pivotably supported on the longitudinal beam of the bearing surface the articulation for the pivoting of the extension beam in the horizontal plane is located on the side of the patient support surface and not on the side of the extension beam. As a result thereof, the articulation can be designed to be very stable without the weight of the extension beam being increased. The elimination of the articulation on the side of the extension beam makes the latter lighter and thus also more convenient to handle. The remote actuation allows, for example the locking device to be actuated from the foot end of the patient. As a result this can be performed by an assistant that is not in the immediate, sterile area of the operation site. As a result, the physician does not have to perform the actuation of the locking device and is also not hindered by other persons during his operating activity.

The locking device can comprise, for example, a toothed segment arranged on the longitudinal beam and comprise a toothed segment for engaging with the first toothed segment and arranged on the coupling part on the support surface side, whereby at least one of the toothed segments can be adjusted in and out of engagement with the particular other toothed segment. The toothed segment arranged on the longitudinal beam is preferably rigid and the toothed segment arranged on the coupling part is preferably movable. The locking device can be constructed in such a manner that the movable toothed segment is pretensioned into its engagement position with the rigid toothed segment and can be moved out into a release position by the remote actuation. The remote actuation can take place via a pressure means, e.g., hydraulically. In a preferred embodiment a piston actuated by pressure means is arranged in the coupling part on the beam side in such a manner that it can enter into an active connection with the locking device when the extension beam is coupled in. Thus, in this instance the connection for the pressure means is located on the coupling part on the beam side.

The managing of the extension beam during coupling and decoupling can be further facilitated in that the coupling part on the support surface side and the coupling part on the beam side are constructed in such a manner that the joining direction during the coupling of the extension beam is substantially horizontal and perpendicular to the direction of the longitudinal beams of the patient support surface. Thus, the extension beam can be coupled from the side, which is significantly simpler than if the coupling part of the extension beam must be inserted into the coupling part on the support surface side underneath the patient already lying on the patient support surface, as is the case, for example, in the solution described in the German utility model 20 2009 013 905 U1. In order to ensure a secure coupling and secure holding of the extension beam the coupling part on the support surface side has, in a preferred embodiment of the invention, a receiving pocket laterally open to the outside for receiving the coupling part on the beam side. The arrangement is made in such a manner that the coupling part on the beam side can be locked in its coupling position on the coupling part on the support surface side.

In order to be able to check, for example the reposition of bone fractures with the aid of the extension device, it is frequently necessary to X-ray the concerned leg of the patient and the extension beam must not hinder the production of the image at this time. To this end the extension beam is produced in a known manner from a material capable of being X-rayed, for example from a composite fibrous substance. This material also allows the extension beam to be given a shape such that it does not hinder the irradiating of the patient's leg or only hinders it as little as possible. Thus, the extension beam can be bent in its length with a first straight section connecting to the coupling part on the beam side which first section is aligned in the coupled state parallel to the longitudinal beam of the patient support surface, with a transitional section bent relative to the first section, and with a second straight section which is again parallel to the first section. As a result, the extension beam is deflected to the side relative to a patient's leg so that it does not appear in the image during an irradiation of the patient's leg in the vertical direction.

In an especially preferred embodiment of the invention the extension beam is constructed in the shape of a tube with an oval cross section, whereby the extension beam is arranged relative to the coupling part on the beam side in such a manner that in the coupled state of the extension beam the longer cross-sectional axis of the oval is inclined relative to the horizontal. The oval cross-sectional form and the orientation of the oval have the result that in an irradiation of the patient's leg which irradiation deviates from the vertical and in which the extension beam can move into the image, the irradiated material of the extension beam corresponds maximally to the double wall strength of the beam. In contrast thereto, in the case of a quadratic cross section of the extension beam it can occur that a part of the rays runs over a rather large length inside the beam wall, so this part of the rays is heavily absorbed by the beam material. The holder for the feed rod unit is advantageously connected at the end of the extension beam that is remote from the patient support surface to this end by a linkage with four articulations, the articulation axes of which are directed in the coupled state of the extension beam horizontally and transversely to the longitudinal direction of the extension beam. The linkage with four articulations allows the feed rod unit and therewith the patient's leg to move on a vertical circular track about the hip joint of the patient without traction or thrust being exerted on the patient's leg.

BRIEF DESCRIPTION OF THE DRAWINGS

The following description explains, in conjunction with the attached drawings, the connection using an exemplary embodiment. In the figures.

DETAILED DESCRIPTION OF THE PREFERRED EMBODIMENT

Figure 1:
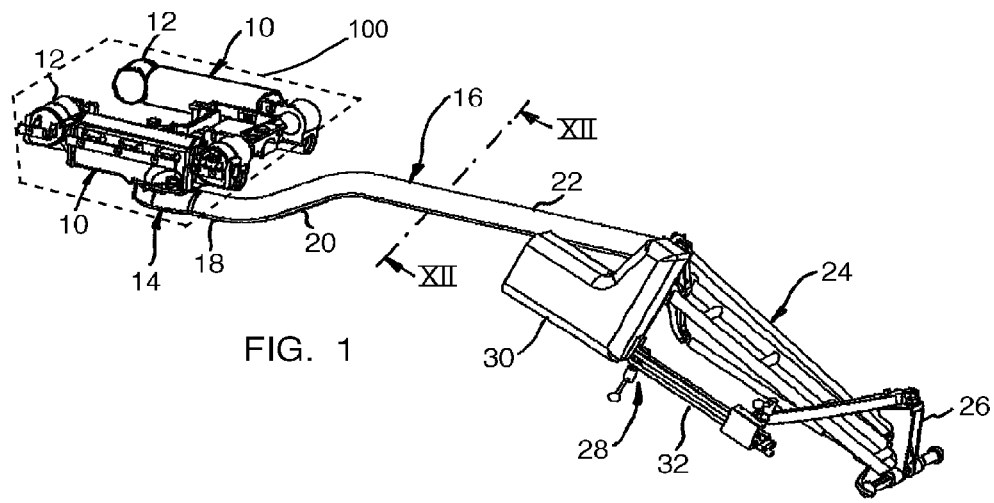
FIG. 1 shows a partial schematic, perspective view of a part of a patient support surface with coupled extension beam and feed rod unit.

The extension device shown in FIG. 1 comprises a schematically shown part of a patient support surface 100 with two support surface beams 10 that are parallel to one another and that each have connection elements 12 on their longitudinal ends for attaching other support surface parts. The support surface beams 10 carry a pelvic plate (not shown) for supporting a patient. An extension beam designated in general with 16 is coupled at an interface 14 to one of the support surface beams 10. The extension beam is formed by a bent tube that comprises a first straight section 18 in the vicinity of the support surface, a bent transitional section 20, and a second section 22 parallel to the first section 18. The tube is manufactured from composite carbon fiber material and has an oval.

Figure 2:
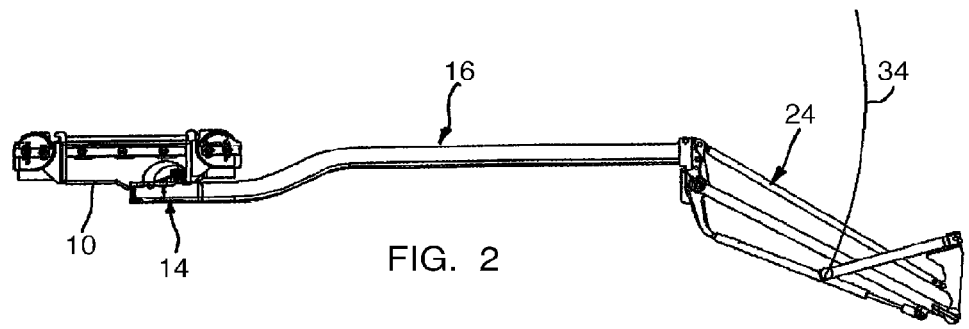
FIG. 2 shows a side view of the extension device according to FIG. 1 without feed rod unit.
Figure 3:
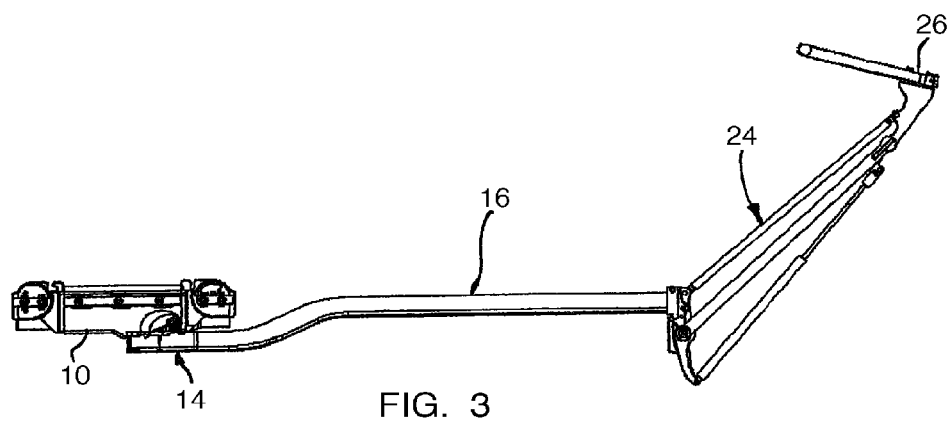
FIG. 3 shows a view, corresponding to FIG. 2, of the extension device with a pivoted holder for the feed rod unit.

The extension beam is connected at its end remote from the support surface section to a linkage 24 with four articulations that carries a holder 26 for a feed rod unit 28. The feed rod unit comprises a shoe 30 for receiving a patient's foot as well as comprises a traction linkage 32 with the aid of which a traction can be exerted on the patient's foot. The connection point of the holder 26 can be moved with the feed rod unit 28 on a circular track 34 (FIG. 2) whose center is the hip joint of the patient with the aid of the four-articulation- or parallelogram linkage 24. As a consequence, the patient's leg can be pivoted up and down in the hip joint without traction being exerted on the patient's leg by the pivoting.

The interface for the coupling of the extension beam 16 with the support surface beam 10 will be explained in detail in the following.

Figure 4:
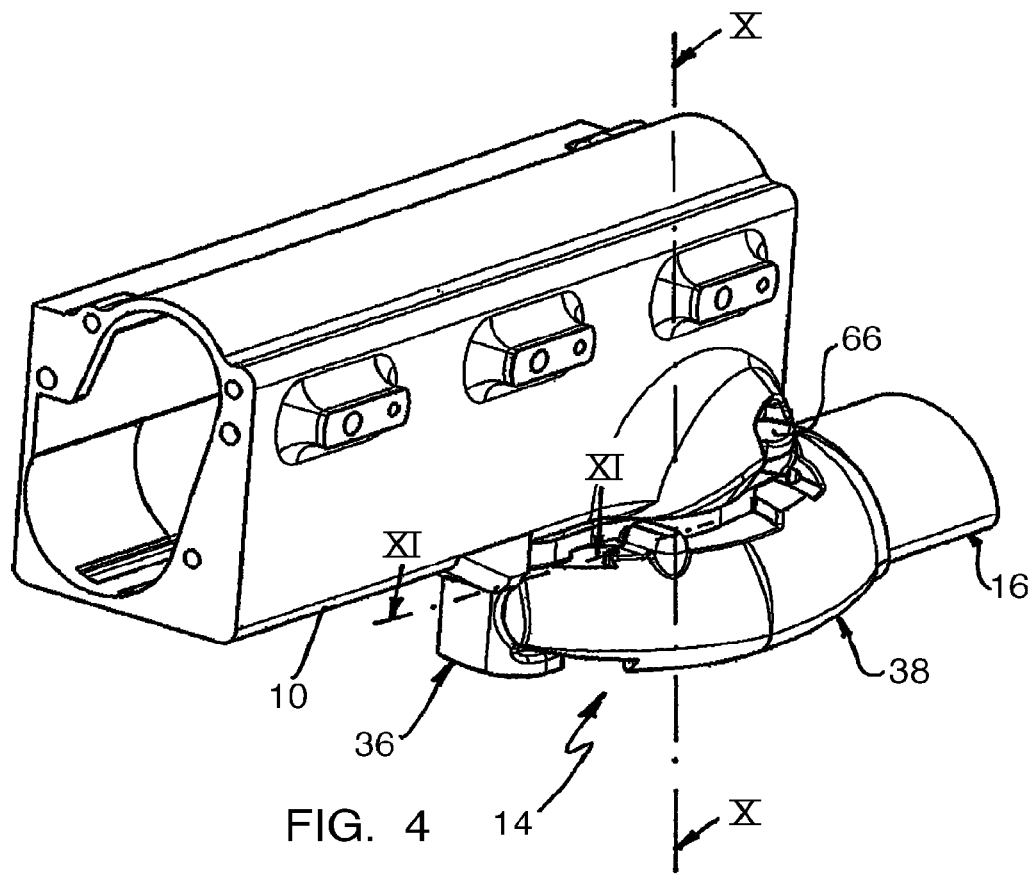
FIG. 4 shows an enlarged perspective view of the support surface beam only with the interface for the coupled extension beam.

FIG. 4 shows the extension beam 10 with the interface 14, that comprises a coupling part 36 on the support surface side and comprises a coupling part 38 on the beam side and connected to the extension beam 16. The coupling part on the support surface side is shown in detail in FIGS. 5 to 7. It is in the form of a block-shaped housing 40 that has a through support opening 42 in its middle by which the coupling part 36 on a rigid pin (not shown) arranged on the bottom of the longitudinal beam 10 is supported in such a manner that it can pivot about the pin axis. This pin support makes possible the pivoting of the coupling part 36 on the support surface side and therewith of the extension beam 16 coupled to it about a vertical axis.

Figure 6:
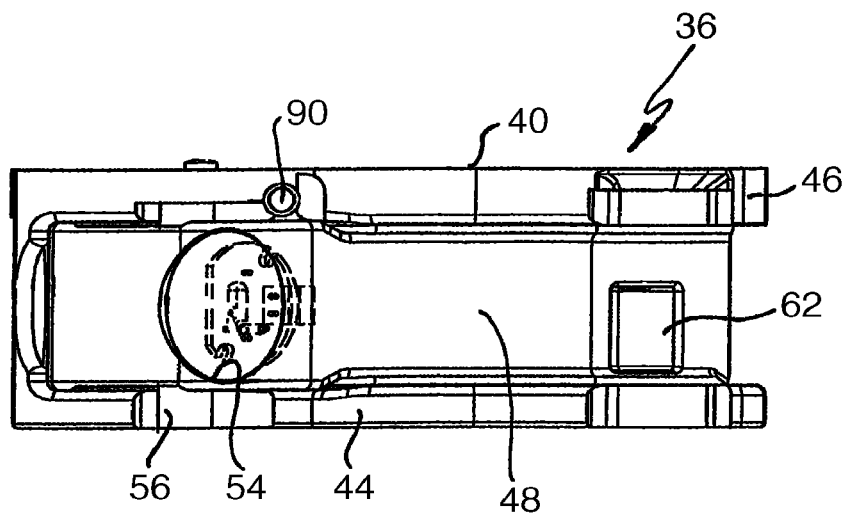
FIG. 6 shows a view of the coupling part on the support surface side in the direction of the arrow A in FIG. 5.
Figure 8:
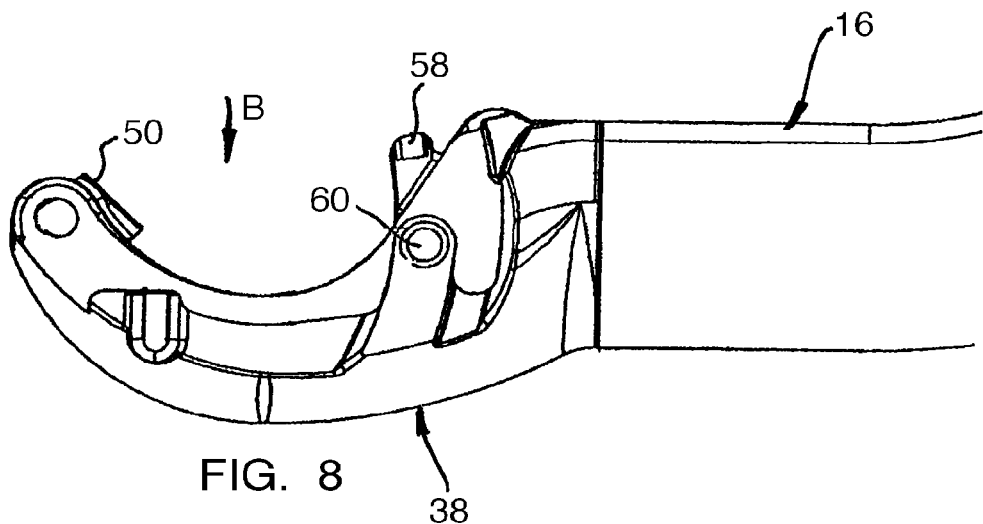
FIG. 8 shows a top view onto the coupling part on the beam side.
Figure 9:
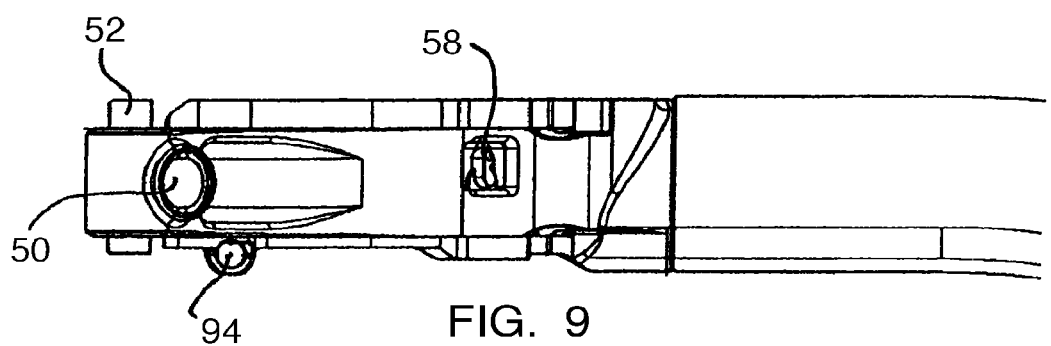
FIG. 9 shows a view of the coupling part on the beam side in the direction of the arrow B in FIG. 8.
Figure 12:
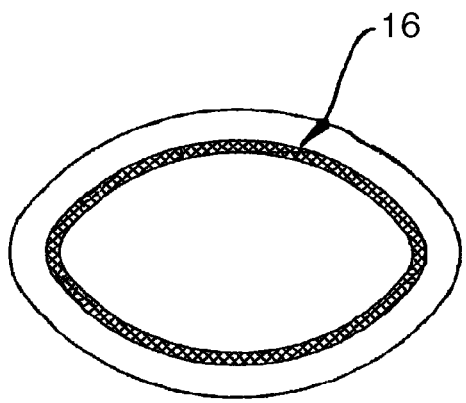
FIG. 12 shows a cross section through the extension beam along line XII-XII in FIG. 1.

The block-shaped housing 40 has on its one side a receiving pocket 48 delimited by a lower flange 44 and an upper flange 46 for receiving the coupling part 38 on the beam side that is shown in FIGS. 8 and 9. It is constructed to be sickle-shaped and has on its free sickle end a flat cylindrical continuation 50 (FIG. 8) on the inside and has a pin 52 that are for engaging into a corresponding circular recess 54 on the bottom of pocket 48 or into a hooked opening 56 provided in the lower flange 44. On its end close to the extension beam 16 the coupling part 38 curved in the shape of a sickle has a catch pawl 58 mounted in such a manner in the coupling part that it can be pivoted by pressure on an actuating pin 60 between a locking position and a release position. The catch pawl 58 is intended for engaging into a catch opening 62 formed on the bottom of the receiving pocket 48 in the coupling part 36 on the support surface side (FIG. 6).

In order to couple the two coupling parts 36 and 38 the coupling part 38 on the beam side is introduced with the pin 52 into the hooked opening 56 on the flange 44 of the coupling part 36 on the support surface side, whereby also the cylindrical continuation 50 enters into the opening 54 on the bottom of the receiving pocket 48. Then, the extension beam 16 is pivoted together with the coupling part 38 about the shaft of the pin 52 in such a manner that the coupling part 38 enters into the receiving pocket 48 and the catch pawl 58 snaps into the catch opening 62. The actuation pin 60 is then in alignment with a bore 64, that is formed in the upper flange 46 of the housing 40. The actuation pin 60 can be actuated through this bore 64 by a pressure key 66 arranged on the support surface beam 10 in order to transfer the catch pawl 58 back into its release position. As FIG. 4 shows, the arrangement is such that the operator puts his hand under the coupling part 38 on the beam side and can actuate the pressure key 66 with his thumb so that during the loosening of the locking by pressing down the pressure key 66 the extension beam 16 can be securely grasped at the same time and can not fall out of the coupling part 36 on the support surface side.

Figure 5:
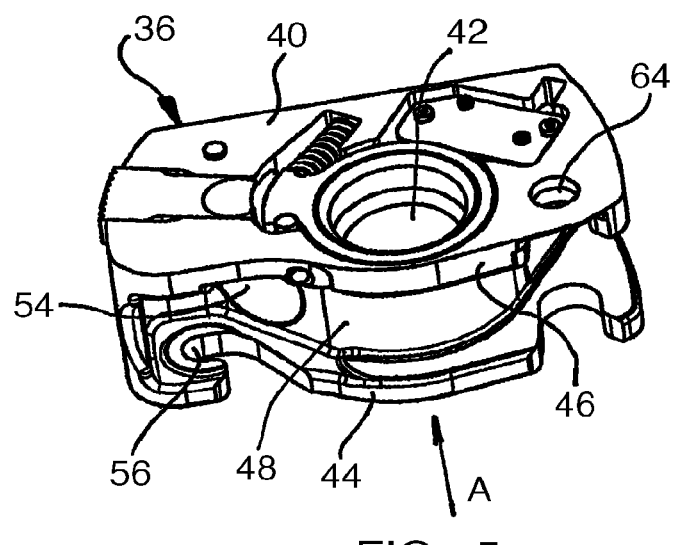
FIG. 5 shows a perspective, partially schematic view of the coupling part on the support surface side.
Figure 7:
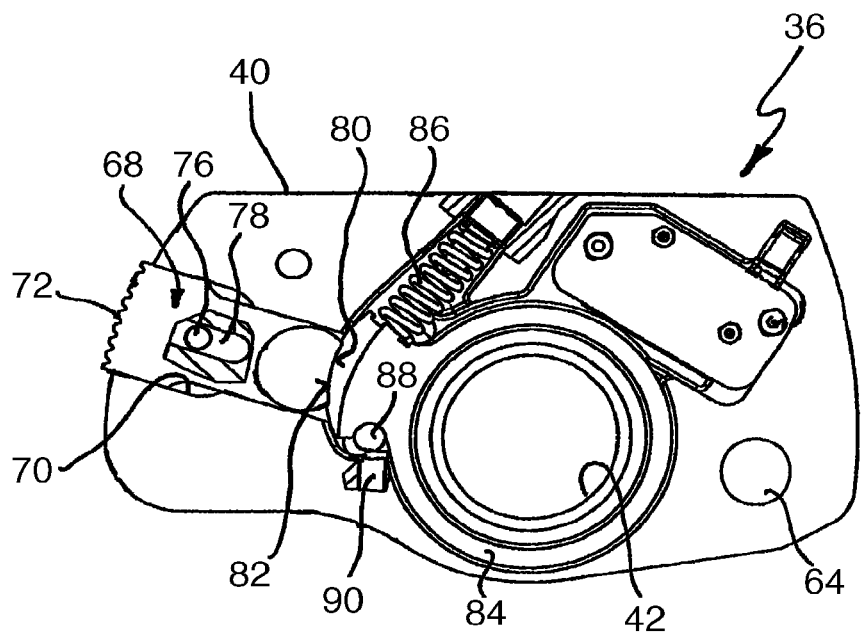
FIG. 7 shows a top view onto the coupling part on the support surface side.
Figures 10, 11:
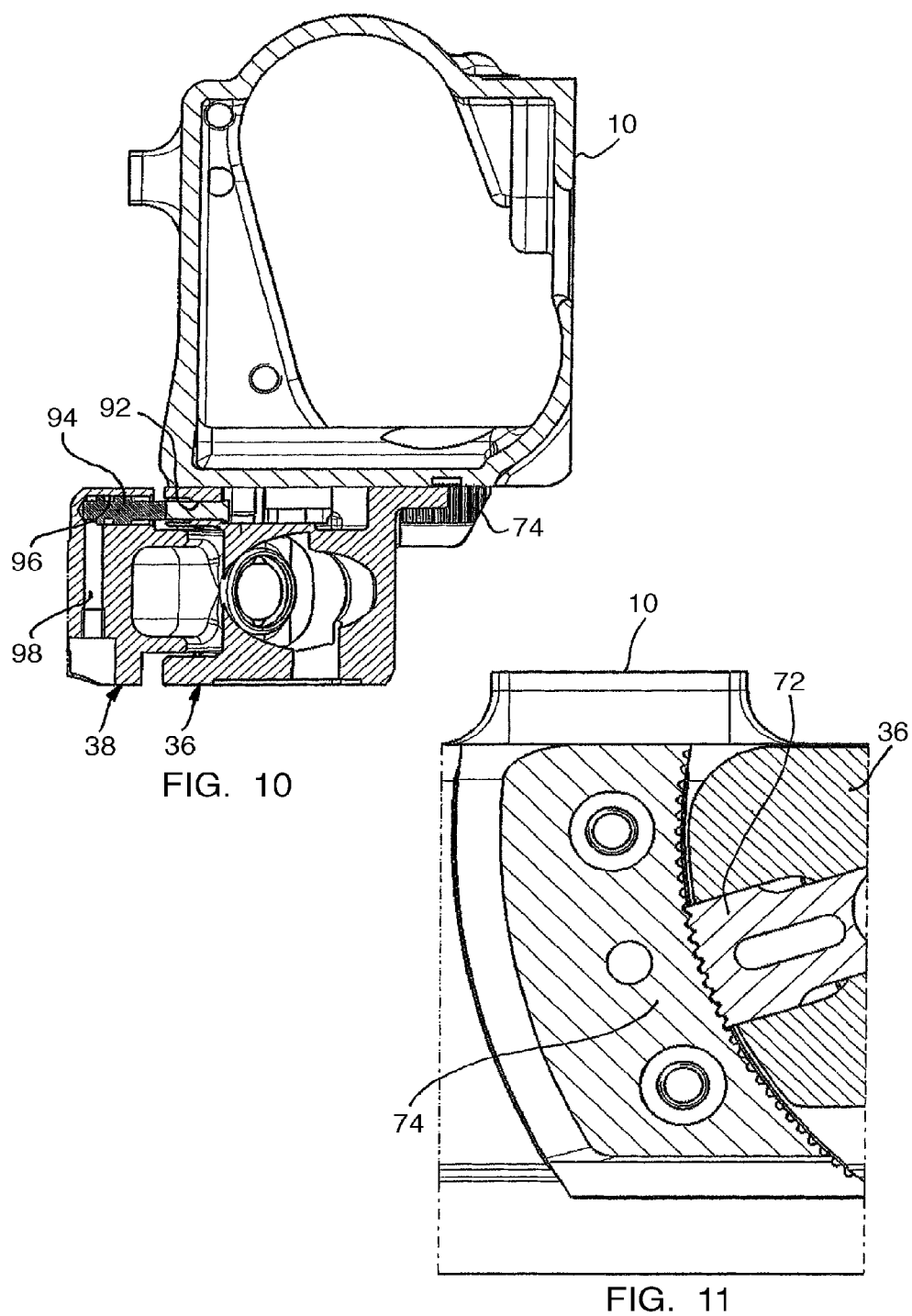
FIG. 10 shows a section through the support surface beam and the interface along line X-X in FIG. 4.
FIG. 11 shows a steep section through the interface along line XI-XI in FIG. 4.

As can be recognized in FIGS. 5 and 7 a slide 68 is shiftably supported in the upper flange 46 of the housing 40 in a flat groove 70 running substantially radially to the passage opening 42. The slide has a toothed segment 72 on its end remote from the passage opening 42 that is intended for engagement with a toothed segment 74 rigidly connected to the longitudinal beam 10 of the patient support surface (as FIG. 11 shows) in order to lock the coupling part 36 on the support surface side in a certain pivot position about the vertical axis. The slide 68 is guided by a pin 76 that is fixed to the housing and engages in a slot 78 of the slide. Furthermore, the slide rests via a cam curve 80 on a cam 82 that is connected to a ring 84 that for its part is supported in such a manner that it can rotate about the support axis of the coupling part 36 on the support surface side, as is shown in particular in FIG. 7. The ring 84 is pretensioned counterclockwise by a compression spring 86 in FIG. 7 and rests with the flank of the cam 82 via a roller 88 on an actuating bolt 90 that is shiftably arranged in a bore 92 (FIG. 10) of the housing 14. If the bolt 90 in FIG. 7 is shifted upward and therefore the ring 84 in FIG. 7 is pivoted clockwise against the pressure of the compression spring 86, the slide 68 moves under the action of the spring (not shown) in the direction of the center of the passage opening 42 so that the toothed segment 72 comes out of engagement with the toothed segment 74. The housing 40, i.e., the coupling part 36 on the support surface side, can then be pivoted about the vertical axis until the bolt 90 is released again and the slide 68 is pressed outward into engagement with the toothed segment 74 under the action of the cam 82 rotating counterclockwise.

The actuation of the bolt 90 takes place in the exemplary embodiment shown hydraulically with the aid of a piston 94 arranged in a cylindrical bore 96 of the coupling part 38 on the beam side in such a manner that it enters into alignment with the actuating bolt 90 during the coupling of the two coupling parts 36, 38. The piston 94 can be moved by a hydraulic fluid that can be supplied through a fluid conduit 98 constructed in the coupling part 38 on the beam side. This makes possible a remote actuation of the locking device 72, 74.

While the present invention has been illustrated and described with respect to a particular embodiment thereof, it should be appreciated by those of ordinary skill in the art that various modifications to this invention may be made without departing from the spirit and scope of the present.

The invention claimed is:

1. An extension device comprising:
a patient support surface; and
an extension beam that connects on its one end via an interface to the patient support surface and that has a holder for a feed rod arrangement on its other end;
wherein the patient support surface has at least two longitudinal beams parallel to each other, the at least two longitudinal beams configured to directly support the patient support surface;
wherein the interface comprises a first coupling part on a patient support surface side of the interface connecting to the patient support surface and comprises a second coupling part rigidly connected to the extension beam on a beam side of the interface;
wherein the first coupling part on the patient support surface side is pivotably supported on one of the at least two longitudinal beams about an axis perpendicular to a plane containing axes of the at least two longitudinal beams;
wherein the first coupling part on the patient support surface side is lockable by a locking device against a rotation about its pivot axis relative to one of the at least two longitudinal beams; and
wherein the locking device is actuated by a remote actuation.

2. The extension device according to claim 1, wherein the locking device comprises a first toothed segment arranged on one of the at least two longitudinal beams and comprises a second toothed segment for engaging with the first toothed segment and arranged on the coupling part on the patient support surface side, whereby at least one of the first or second toothed segments is adjustable in and out of engagement with the particular other first or second toothed segment.

3. The extension device according to claim 2, wherein the first toothed segment arranged on one of the at least two longitudinal beams is rigid and the second toothed segment arranged on the coupling part is movable.

4. The extension device according to claim 3, wherein the movable toothed segment is pretensioned into its engagement position with the rigid toothed segment and is movable out into a release position by the remote actuation.

5. The extension device according to claim 1, wherein the extension beam consists of a material capable of being X-rayed.

6. The extension device according to claim 5, wherein the extension beam is constructed as a tube with an oval cross section.

7. The extension device according to claim 5, wherein the extension beam is bent with a first straight section following the coupling part on the beam side; the first straight section being aligned in a coupled state parallel to the at least two longitudinal beams of the patient support surface, with a transitional section bent relative to the first straight section, and with a second straight section which is parallel to the first straight section.

8. The extension device according to claim 1, wherein the first coupling part on the patient support surface side and the second coupling part on the beam side are constructed in such a manner that a joining direction during the coupling of the extension beam is substantially horizontal and vertical to a direction of the at least two longitudinal beams of the patient support surface.

9. The extension device according to claim 8, wherein the coupling part on the patient support surface side has a receiving pocket laterally open to an outside for receiving the coupling part on the beam side.

10. The extension device according to claim 1, wherein the remote actuation takes place via a pressure fluid.

11. The extension device according to claim 1, wherein the coupling part on the beam side is lockable in its coupling position on the coupling part on the patient support surface side.

12. The extension device according to claim 1, wherein the holder for the feed rod arrangement is connected to the extension beam by a linkage with four articulations whose articulation axis is directed in a coupled state of the extension beam horizontally and transversely to a longitudinal direction of the extension beam.

13. The extension device according to claim 1, wherein a piston, actuated by a hydraulic device disposed at the second coupling part on the beam side, is arranged in such a manner that it enters into an active connection with the locking device when the extension beam is coupled to the patient support surface at the interface.

14. An extension device comprising:
a patient support surface; and
an extension beam that connects on its one end via an interface to the patient support surface and that has a holder for a feed rod arrangement on its other end;
wherein the patient support surface has at least two longitudinal beams parallel to each other;
wherein the interface comprises a first coupling part on a patient support surface side of the interface connecting to the patient support surface and comprises a second coupling part rigidly connected to the extension beam on a beam side of the interface;
wherein the first coupling part on the patient support surface side is pivotably supported on one of the at least two longitudinal beams about an axis perpendicular to a plane containing axes of the at least two longitudinal beams;
wherein the first coupling part on the patient support surface side is lockable by a rotational locking device against a rotation about its pivot axis relative to one of the at least two longitudinal beams; and
wherein the rotational locking device disposed adjacent to the patient support surface is actuated by a remote actuation.

15. The extension device according to claim 14, wherein the extension beam is aligned relative to the second coupling part on the beam side in such a manner that in a coupled state a longest cross-sectional axis of an oval cross section of the extension beam is inclined relative to a horizontal axis.

16. The extension device according to claim 14, wherein the remote actuation includes remote hydraulic actuation of a piston.

17. The extension device according to claim 14, wherein the rotational locking device comprises a first toothed segment arranged on one of the at least two longitudinal beams and comprises a second toothed segment for engaging with the first toothed segment and arranged on the first coupling part on the patient support surface side, whereby at least one of the first or second toothed segments is adjustable in and out of engagement with the particular other first or second toothed segment.

18. An extension device comprising:
a patient support surface; and
an extension beam that connects on its one end via an interface to the patient support surface and that has a holder for a feed rod arrangement on its other end;
wherein the patient support surface has at least two longitudinal beams parallel to each other;
wherein the interface comprises a first coupling part on a patient support surface side of the interface connecting to the patient support surface and comprises a second coupling part rigidly connected to the extension beam on a beam side of the interface;
wherein the first coupling part is disposed adjacent to the patient support surface and is pivotably supported on one of the at least two longitudinal beams about an axis perpendicular to a plane containing axes of the at least two longitudinal beams;
wherein the first coupling part on the patient support surface side is lockable by a locking device against a rotation about its pivot axis relative to one of the at least two longitudinal beams; and
wherein the locking device is actuated by a remote actuation.

19. The extension device according to claim 18, wherein the extension beam consists of a composite fibrous substance.

20. The extension device according to claim 18, wherein the at least two longitudinal beams are fixed parallel to each other.

* * * * *